United States Patent [19]
Nakano et al.

[11] Patent Number: 5,482,524
[45] Date of Patent: Jan. 9, 1996

[54] ATMOSPHERIC PRESSURE, ELEVATED TEMPERATURE GAS DESORPTION APPARATUS

[75] Inventors: Kazuo Nakano, Sendai; Kazuaki Mizokami, Kodaira; Keiji Hasumi, Iruma; Katsuhiko Itoh, Tokyo; Michimasa Funabashi; Yasuhiro Mitsui, both of Fuchu; Takashi Irie, Kokubunji; Takeshi Tajima, Tokyo; Sadao Matsuoka, Kanagawa, all of Japan

[73] Assignees: Hitachi, Ltd.; Hitachi Tokyo Electronics Co., Ltd., both of Tokyo, Japan

[21] Appl. No.: 285,421

[22] Filed: Aug. 3, 1994

[30] Foreign Application Priority Data

Sep. 16, 1993 [JP] Japan .................................. 5-229894

[51] Int. Cl.[6] ............................ B01D 53/04; B01D 35/18
[52] U.S. Cl. ................................ 55/267; 55/270; 96/141; 96/144
[58] Field of Search ........................ 55/267, 270; 96/101, 96/105, 108, 141, 144

[56] References Cited

U.S. PATENT DOCUMENTS

| 4,321,822 | 3/1982 | Marple et al. | 55/270 X |
| 4,650,499 | 3/1987 | Scott | 55/270 X |
| 4,725,294 | 2/1988 | Berger | 55/270 |

OTHER PUBLICATIONS

"Out Gas Free Resist Process", VLSI Ultra–Clean Technology Workshop. No. 5, Ultra–Clean Resist Processing, Jun. 28, 1990.

*Primary Examiner*—Robert Spitzer
*Attorney, Agent, or Firm*—Fay, Sharpe, Beall, Fagan, Minnich & McKee

[57] ABSTRACT

An atmospheric pressure, elevated temperature gas desorption apparatus which enables quanitiative analysis of impurities absorbed in or on the surface of a solid sample (semiconductor wafer, optical disc, etc.) is disclosed. The atmospheric pressure, elevated temperature gas desorption apparatus for desorbing impurities absorbed in or on the surface of a plate-like solid sample 18 into a carrier gas 19 in a chamber 6 under an atmospheric pressure while increasing the temperature of the solid sample 18 includes a desorption room 7A provided in the chamber 6 and connected through to a first gas supply system 1 for supplying the carrier gas 19, for desorbing impurities absorbed in or on the surface of the solid sample 18 into the carrier gas 19. A sample support room 7B is provided in the chamber 6 and is separated from the desorption room 7A by a partition member 6A. The solid sample 18 is in close contact with the partition member 6A. A heater 8 for heating the solid sample 18 is in close contact with the partition member 6A. A reserve room 9 is connected to the sample support room 7B and to a second gas supply system 13 for supplying a purge gas.

12 Claims, 11 Drawing Sheets

ATMOSPHERIC PRESSURE, ELEVATED TEMPERATURE GAS DESORPTION APPARATUS

BACKGROUND OF THE INVENTION

The present invention relates to a technique that is effectively applied to an atmospheric pressure, elevated temperature desorption apparatus which increases the temperature of a plate-like solid sample (semiconductor wafer, optical disc, etc.) and desorb impurities (substances of an extremely small amount) that are absorbed in or on the surface of the solid sample into a carrier gas under an atmospheric pressure.

In semiconductor manufacturing technologies, among apparatuses for analyzing impurities (substances of an extremely small amount) absorbed in or on the surface of a semiconductor wafer that has been subjected to respective manufacturing processes, there is known, for instance, an ultra-high vacuum, elevated temperature desorbed gas analyzing apparatus that is described in Vacuum, Vol. 34, No. 11 (1991), pp. 813–819. In this ultra-high vacuum, elevated temperature desorbed gas analyzing apparatus, a semiconductor wafer is divided into small square sections of 1 cm×1 cm and their temperature is elevated in an ultra-high vacuum chamber, and gases desorbed from the semiconductor wafer are analyzed.

As another example, there is known a sample column that is described on Page 61 of "Out Gas Free Resist Process," VLSI Ultra-clean Technology Workshop No. 5, Ultra-clean Resist Processing, Jun. 28, 1990. In this apparatus, a semiconductor wafer is divided into small strips and their temperature is elevated under the atmospheric pressure, and gases desorbed from the semiconductor wafer are analyzed.

However, the conventional techniques have the following problems.

(1) When a semiconductor wafer is divided into small square sections or strips, contaminants (other impurities) attach to the semiconductor wafer. Therefore, the quantitative analysis of impurities originally absorbed in or on the surface of the semiconductor wafer cannot be performed correctly.

(2) When a semiconductor wafer is introduced into a chamber, the external air flows into the chamber to cause contaminants (other impurities) to stick to the inside of the chamber. Therefore, the quantitative analysis of impurities originally absorbed in or on the surface of the semiconductor wafer cannot be performed correctly.

(3) Since there occurs variations in a temperature distribution of a heated semiconductor wafer, the quantitative analysis of impurities originally absorbed in or on the surface of the semiconductor wafer cannot be performed correctly.

(4) Since the front surface and the back surface of a semiconductor wafer cannot be processed separately, the quantitative analysis of impurities originally absorbed in or on the front surface of the semiconductor wafer cannot be performed.

(5) When a semiconductor wafer is moved into a chamber from each manufacturing process, the semiconductor wafer is contaminated by the air. Therefore, the quantitative analysis of impurities originally absorbed in or on the surface of the semiconductor wafer cannot be performed correctly.

SUMMARY OF THE INVENTION

An object of the present invention is to provide an atmospheric pressure, elevated temperature gas desorption apparatus which can perform quantitative analysis of impurities absorbed in or on the surface of a solid sample (semiconductor wafer, optical disc, etc.).

The above and other objects and novel features of the invention will be apparent from the description of this specification and the accompanying drawings.

Representative parts of the invention disclosed in this application will be briefly summarized below.

(1) An atmospheric pressure, elevated temperature gas desorption apparatus for desorbing impurities absorbed in or on a surface of a plate-like solid sample into a carrier gas in a chamber under an atmospheric pressure while increasing a temperature of the solid sample, includes a desorption room provided in the chamber and connected through a pipe to a first gas supply system for supplying the carrier gas, for desorbing impurities absorbed in or on the surface of the solid sample into the carrier gas supplied from the first gas supply system, a sample support room provided in the chamber and to be separated from the desorption room by a partition member and the solid sample being brought in close contact with the partition member, for incorporating a sample support for conveying and supporting the solid sample to be brought in close contact with the partition member, a heater for heating the solid sample being brought in close contact with the partition member, and a reserve room connected to the sample support room and connected through a supply pipe to a second gas supply system for supplying a purge gas, for reserving the solid sample to be conveyed to the sample support room.

(2) The reserve room has an inlet for introducing the solid sample from the exterior, which inlet has such a size as produces a gap between the inlet and the solid sample.

(3) The heater includes an infrared lamp, and an infrared diffusing plate is disposed between the infrared lamp and the desorption room.

(4) A gas diffusing member for diffusing the carrier gas is disposed in the vicinity of a supply inlet of the desorption room through which the carrier gas is supplied.

(5) First and second shutters are provided for the reserve room and the sample support room, respectively to separate those rooms from each other.

(6) An atmospheric pressure, elevated temperature gas desorption apparatus for desorbing impurities absorbed in or on a surface of a plate-like solid sample into a carrier gas in a chamber under an atmospheric pressure while increasing a temperature of the solid sample, comprises a first desorption room provided in the chamber and connected through a first pipe to a gas supply system for supplying the carrier gas, for desorbing impurities absorbed in or on a front surface of the solid sample into the carrier gas supplied from the gas supply system, a second desorption room provided in the chamber, to be separated from the first desorption room by a partition member and the solid sample being brought in close contact with the partition member, and connected through a second pipe to the gas supply system for supplying the carrier gas, for desorbing impurities absorbed in or on a back surface of the solid sample that is opposed to the front surface into the carrier gas supplied from the gas supply system, and a heater for heating the solid sample being brought in close contact with the partition member.

According to the above-described means (1), since impurities absorbed in or on the surface of the plate-like solid sample in its original state (i.e., not divided into small pieces) can be desorbed into the carrier gas, contaminants that would be introduced at the time of dividing are prevented from being mixed into the carrier gas. Therefore, the quantitative analysis of impurities absorbed in or on the surface of the solid sample can be performed correctly.

Further, impurities absorbed in or on the surface of the solid sample are desorbed into the carrier gas after preliminary heating is performed by the heater in the state that the solid sample stands by in the reserve room to which the purge gas is supplied from the second gas supply system and contaminants (other impurities) attaching to the inner surfaces of the chamber have been removed. Therefore, contaminants can be prevented from being mixed into the carrier gas, thus enabling the quantitative analysis of impurities absorbed in or on the surface of the solid sample to be performed correctly.

Further, since impurities absorbed in or on only the one surface of the solid sample that is exposed to the desorption room can be desorbed into the carrier gas, the front surface and the back surface of the solid sample can be processed separately. As a result, the quantitative analysis of impurities absorbed in or on the surface of the solid sample can be performed correctly.

According to the above-described means (2), since the solid sample is introduced into the reserve room from the exterior through the inlet while the purge gas is jetted out from the reserve room by making the pressure of the purge gas being supplied to the reserve room higher than the atmospheric pressure, can be prevented from contaminants coming from the exterior attach to the inner surface of the reserve room. Therefore, the quantitative analysis of impurities absorbed in or on the one surface of the solid sample can be performed correctly.

Further, since the reserve room is preliminarily heated by the preliminary heater and contaminants attaching to the inner surface of the reserve room are expelled, contaminants can be removed before the introduction of the solid sample. Therefore, the quantitative analysis of impurities absorbed in or on the one surface of the solid sample can be performed correctly.

According to the above-described means (3), since the surface of the solid sample is uniformly illuminated with infrared light, variations in the temperature distribution of the solid sample can be prevented. Therefore, the quantitative analysis of impurities absorbed in or on the one surface of the solid sample can be performed correctly.

According to the above-described means (4), since the carrier gas supplied is diffused to uniformly impinges on the surface of the solid sample, variations in the temperature distribution of the solid sample can be prevented. Therefore, the quantitative analysis of impurities absorbed in or on the one surface of the solid sample can be performed correctly.

According to the above-described means (5), the solid sample can be introduced from each manufacturing process included the manufacturing process line to the sample support room without being exposed to the external air. Therefore, impurities absorbed in or on the one surface of the solid sample can be desorbed into the carrier gas without being influenced by the background due to contaminants of the external air. This enables the quantitative analysis of impurities absorbed in or on the surface of the solid sample to be performed correctly, According to the above-described means (6), impurities absorbed in or on the front surface of the solid sample are desorbed into the one carrier gas while impurities absorbed in or on the back surface of the solid sample are desorbed into the other carrier gas, Therefore, impurities absorbed in or on the front and back surfaces of the solid sample can be desorbed separately.

DESCRIPTION OF THE PREFERRED EMBODIMENTS

Embodiments of the present invention will be hereinafter described with reference to the accompanying drawings.

In all the drawings illustrating the embodiments, the parts having the same functions are given the same reference symbols and redundant descriptions therefor will be avoided.

Embodiment 1

Figure 1:
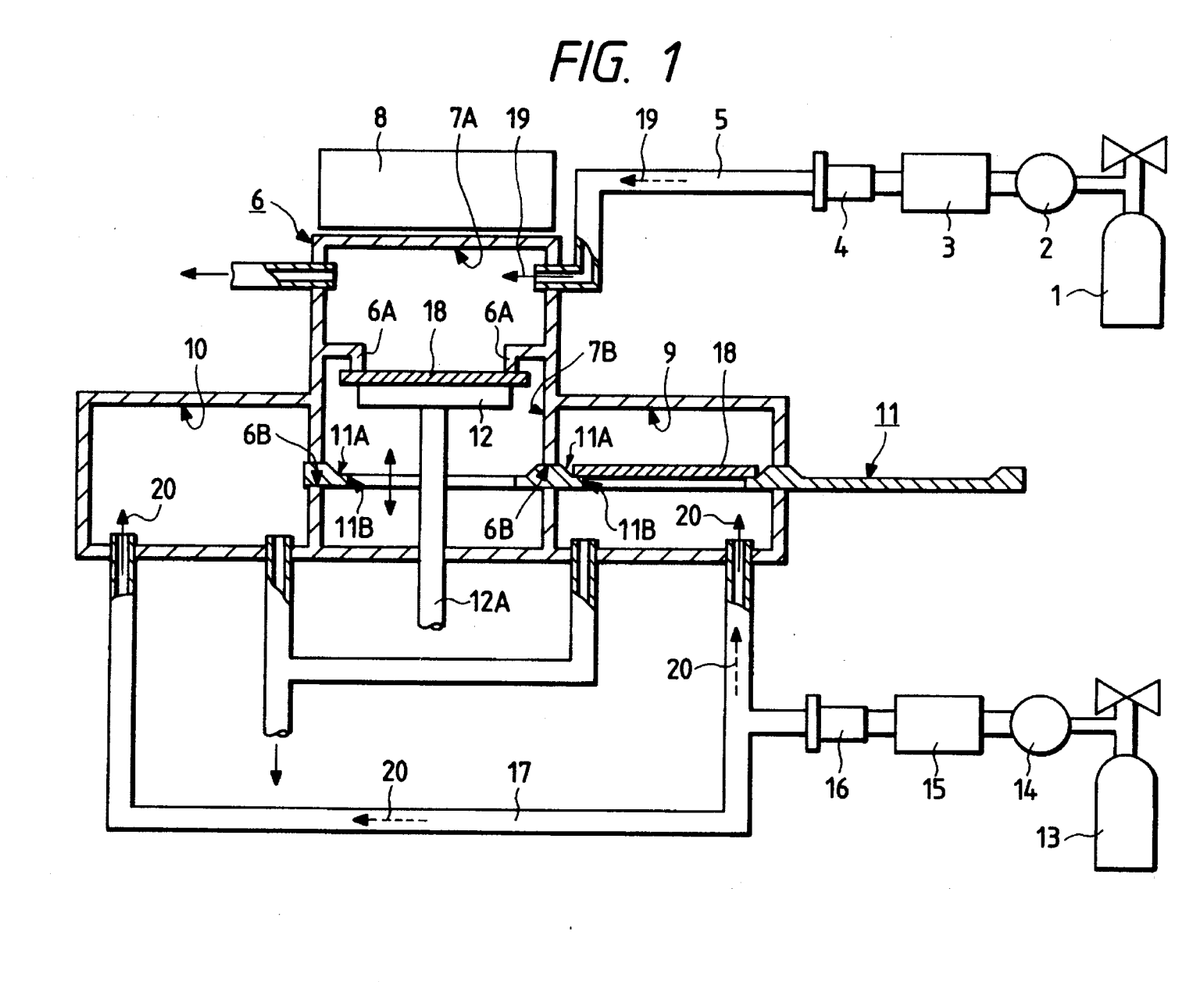
FIG. 1 is a schematic diagram showing a general configuration of an atmospheric pressure, elevated temperature gas desorption apparatus according to a first embodiment of the present invention.

FIG. 1 (schematic diagram) shows a general configuration of an atmospheric pressure, elevated temperature gas desorption apparatus which is a first embodiment of the invention.

As shown in FIG. 1, the atmospheric pressure, elevated temperature gas desorption apparatus of this embodiment has a gas supply system 1 (a pure gas cylinder), a pressure regulator 2, a flow rate regulator 3, a molecular sieve trap 4, a chamber 6, a desorption room 7A, a sample support room 7B, a heater 8, reserve rooms 9 and 10, a conveyor 11, a sample support 12, a gas supply system 13 (pure gas cylinder), a pressure regulator 14, a flow rate regulator 15, a molecular sieve trap 16, and other parts.

The gas supply system 1 is connected to the desorption room 7A through a pipe 5, and supplies a carrier gas 19 to the desorption room 7A. The carrier gas 19 is an inert gas such as $N_2$ or Ar. The pressure regulator 2, flow rate regulator 3 and molecular sieve trap 4 are attached to the pipe 5 between the gas supply system 1 and the desorption room 7A. The pressure regulator 2 keeps the carrier gas 19 at a constant pressure, and the flow rate regulator 3 keeps it at a constant flow rate. The molecular sieve trap 4 removes impurities such as moisture and organic substances from the carrier gas 19.

The gas supply system 13 is connected to each of the reserve rooms 9 and 10 through a pipe 17, and supplies a purge gas 20 to the reserve rooms 9 and 10. The purge gas 20 is an inert gas such as $N_2$ and Ar. The pressure regulator 14, flow rate regulator 15 and molecular sieve trap 16 are attached to the gas supply system 13 and the reserve rooms 9 and 10. The pressure regulator 14 keeps the purge gas 20 at a constant pressure, and the flow rate regulator 15 keeps it at a constant flow rate. The molecular sieve trap 16 removes impurities such as moisture and organic substances from the purge gas 20.

In the desorption room 7A, impurities absorbed in or on the surface of a plate-like solid sample 18 are desorbed into the carrier gas 19. The desorption room 7A is formed in the chamber 6, and is separated from the sample support room 7B by a partition member 6A that is provided in the chamber 6 and the solid sample 18 that is to be brought in close contact with the partition member 6A. The chamber 6 is formed of quartz glass, for instance. The plate-like solid sample 18 is, for instance, a semiconductor wafer or an optical disc.

The sample support room 7B is formed in the chamber 6, and is separated from the desorption room 7A by the partition member 6A and the solid sample 18 when the latter is brought in close contact with the partition member 6A. The sample support 12 for supporting the solid sample 18 and making it in close contact with the partition member 6A is provided in the sample support room 7B.

Being disposed above the desorption room 7A, the heater 8 heats the solid sample 18 being in close contact with the partition member 6A to desorb impurities absorbed in or on the one surface of the solid sample 18.

The reserve rooms 9 and 10 are disposed outside the chamber 6, and communicate with the sample support room 7B through communication paths 6B of the chamber 6, respectively.

The conveyor 11 conveys the solid sample 18 from either of the reserve room 9 and 10 to the chamber 6 through the communication path 6B, or vice versa. For example, two mounting regions 11A on which to mount the solid sample 18 are provided in the conveyor 11 along the conveying direction. A through-hole 11B is formed in a central portion of each of the two mounting regions 11A so as to allow the sample support 12 pass through itself vertically. The conveyor 11 is made of, for instance, ceramics to endure a high temperature.

Figure 2:
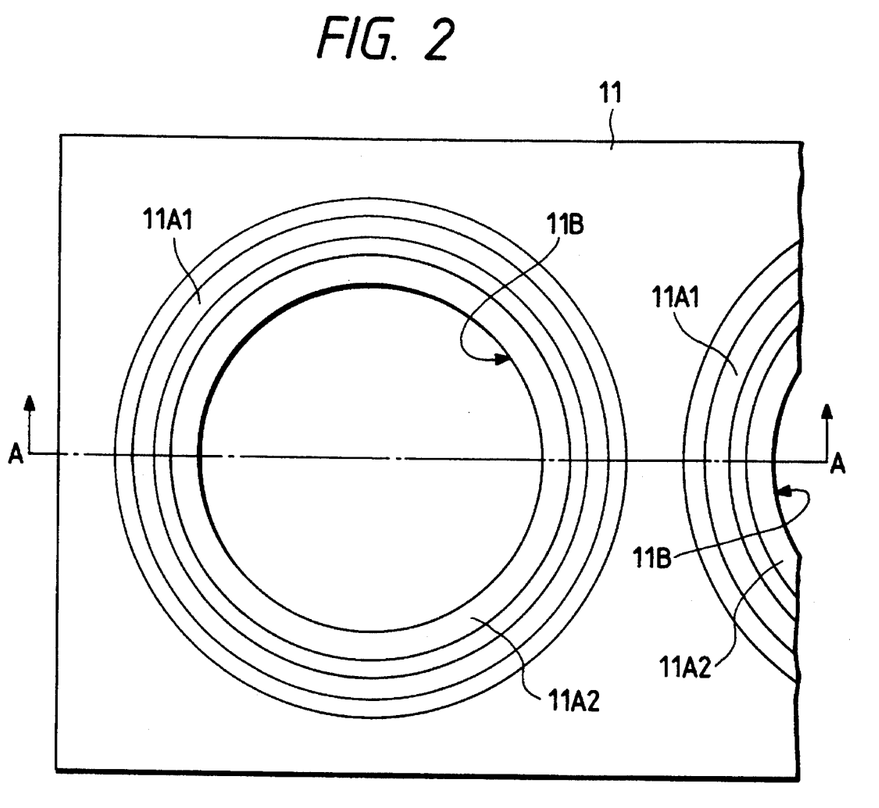
FIG. 2 is a plan view of the main part of a conveyor that is incorporated in the above atmospheric pressure, elevated temperature gas desorption apparatus.
Figure 3:
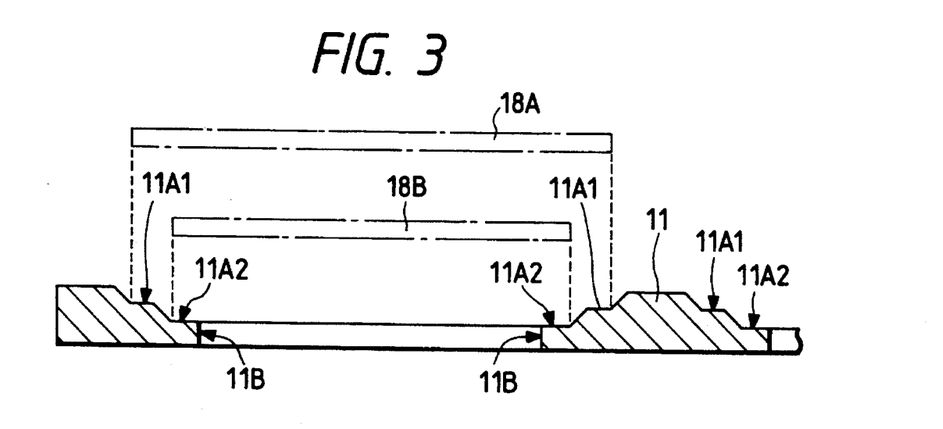
FIG. 3 is a sectional view taken along line A—A in FIG. 2.

As shown in FIG. 2 (a plan view of the main part) and FIG. 3 (a sectional view taken along line A—A in FIG. 2), the sample support 11 may have a stack structure consisting of a mounting region 11A1 which can receive, for instance, a 6-inch solid sample 18A and a mounting region 11A2 which can receive, for instance, a 5-inch solid sample 18B. This structure allows solid samples 18 having different outer sizes to be conveyed.

The sample support 12 is provided in the sample support room 7B, i.e., in the chamber 6, and is fixed to a vertically movable support member 12A. The sample support 12 receives the sample 18 that has been conveyed into the chamber 6 by the conveyor 11, moves the solid sample 18 upward while passing through the through-hole 11B of the conveyer 11, and makes the solid sample 18 in close contact with the partition member 6A.

Next, the operation of the above atmospheric pressure, elevated temperature gas desorption apparatus will be described.

First, the carrier gas 19 is supplied from the gas supply system 1 to the desorption room 7A through the pipe 5. The pressure and flow rate of the carrier gas 19 are respectively regulated to constant values by the pressure regulator 2 and the flow rate regulator 3, and impurities such as moisture and organic substances are removed from the carrier gas 19 by the molecular sieve trap 4.

Then, a solid sample 18 to be used for preliminary heating is made in close contact with the partition member 6A by the sample support 12 to separate the desorption room 7A from the sample support room 7B. In this state, another solid sample 18 to be used for analysis is reserved in the reserve room 9. The purge gas 20 is supplied from the gas supply system 13 to the reserve rooms 9 and 10 through the pipe 17. The pressure and flow rate of the purge gas 20 are respectively regulated to constant values by the pressure regulator 14 and the flow rate regulator 15, and impurities such as moisture and organic substances are removed from the purge gas 20 by the molecular sieve trap 16.

Then, in the state that the desorption room 7A is separated from the sample support room 7B by the solid sample 18 for preliminary heating and the solid sample 18 for analysis stands by in the reserve room 9, the preliminary heating is performed by the heater 8. The preliminary heating serves to remove impurities attaching to the inner surfaces of the chamber 6 (desorption room 7A and sample support room 7B). The temperature of the solid sample 18 for preliminary heating is thereafter reduced to the room temperature (normal temperature).

Then, after the sample support 12 is lowered and the solid sample 18 for preliminary heating is mounted on the mounting region 11A of the conveyor 11, the conveyor 11 is moved so as to forward the solid sample 18 for preliminary heating to the reserve room 10 and introduce the solid sample 18 for analysis into the sample support room 7B.

Finally, the sample support 12 is elevated to make the solid sample 18 for analysis in close contact with the partition member 6A. In this state, heating is performed by the heater 8 to desorb impurities that are absorbed in or on the one surface of the solid sample 18 for analysis into the carrier gas 19.

As described above, according to this embodiment, impurities absorbed in or on the surface of the solid sample 18 can be desorbed into the carrier gas 19 in the state that the solid sample 18 is in its original state, i.e., not divided into small pieces. Therefore, contaminants are prevented from mixing into the carrier gas 19 to enable the quantitative analysis of impurities absorbed in or on the surface of the solid sample 18 to be performed correctly.

Impurities absorbed in or on the surface of the solid sample 18 are desorbed into the carrier gas 19 after the preliminary heating is performed by the heater 8 in the state that the solid sample 18 stands by in the reserve room 9 to which the purge gas 20 is supplied from the gas supply system 13 and contaminants attaching to the inner surfaces of the chamber 6 have been removed. Therefore, that contaminants are prevented from mixing into the carrier gas 19 to enable the quantitative analysis of impurities absorbed in or on the surface of the solid sample 18 to be performed correctly.

Since impurities absorbed in or on only the one surface of the solid sample 18 that is exposed to the desorption room 7A can be desorbed into the carrier gas 19, the front surface and the back surface of the solid sample 18 can be processed separately. As a result, the quantitative analysis of impurities absorbed in or on the surface of the solid sample 18 can be performed correctly.

Embodiment 2

Figure 4:
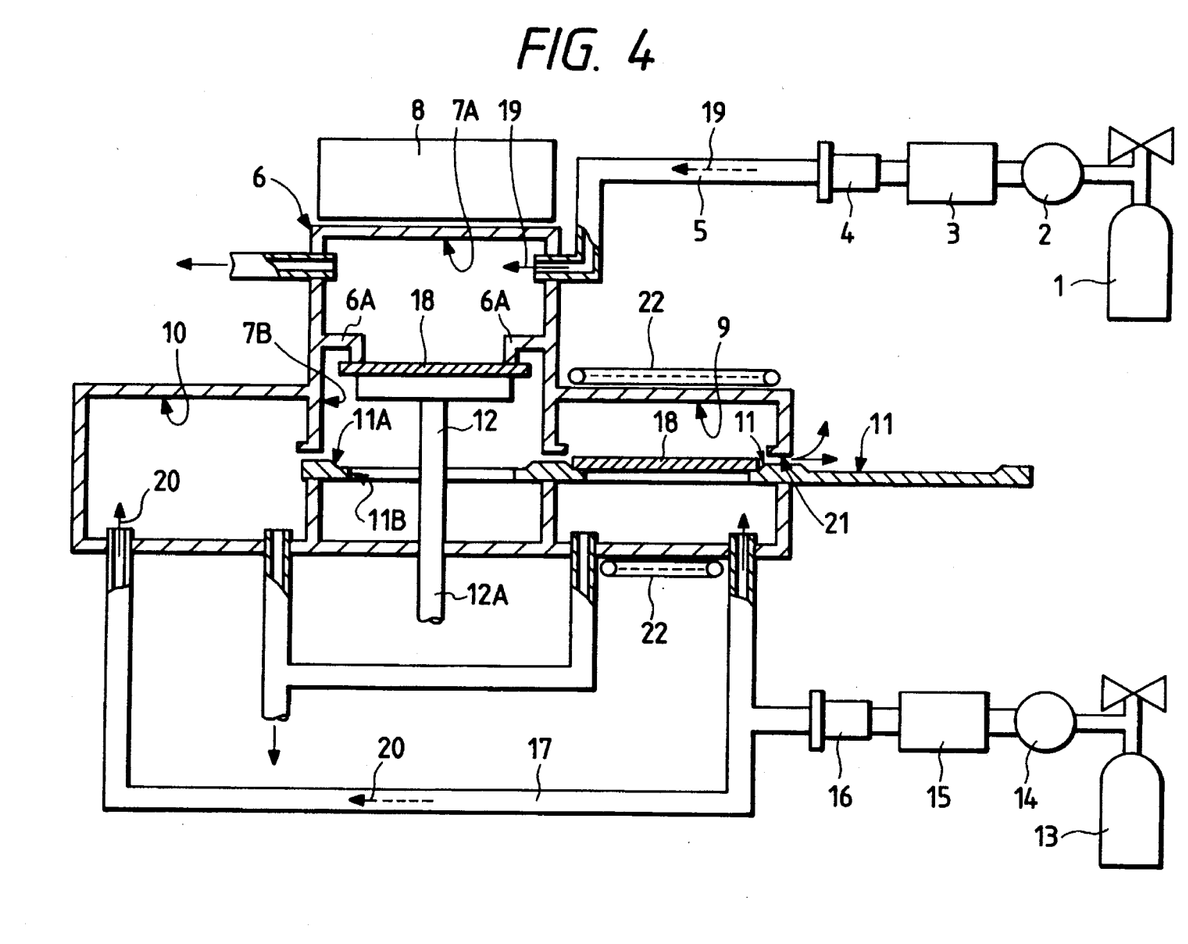
FIG. 4 is a schematic diagram showing a general configuration of an atmospheric pressure, elevated temperature gas desorption apparatus according to a second embodiment of the invention.

FIG. 4 (schematic diagram) shows a general configuration of an atmospheric pressure, elevated temperature gas desorption apparatus which is a second embodiment of the invention.

As shown in FIG. 4, as in the case of the first embodiment, the atmospheric pressure, elevated temperature gas desorption apparatus of this embodiment has a gas supply system 1 (a pure gas cylinder), a pressure regulator 2, a flow rate regulator 3, a molecular sieve trap 4, a chamber 6, a desorption room 7A, a sample support room 7B, a heater 8, reserve rooms 9 and 10, a conveyor 11, a sample support 12, a gas supply system 13 (pure gas cylinder), a pressure regulator 14, a flow rate regulator 15, a molecular sieve trap 16, and other parts.

The reserve room 9 has an inlet 21 through which to receive the solid sample 18 from the exterior. The inlet 21 is so formed as to have a clearance of about 0.5 mm with respect to the solid sample 18 that is mounted on the conveyor 11. A preliminary heater 22 is disposed above the reserve room 9.

The atmospheric pressure, elevated temperature gas desorption apparatus having the above configuration operates in the following manner. Before a solid sample 18 for analysis is introduced into the reserve room 9, the reserve room 9 is heated by the preliminary heater 22 to remove impurities attaching to the inner surface of the reserve room 9. The solid sample 18 for analysis is thereafter introduced into the reserve room 9 through the inlet 21, during which operation the pressure of the purge gas 20 in the reserve room 9 is set higher than the atmospheric pressure so that the purge gas 20 is jetted out from the inlet 21 to prevent the external air from entering into the reserve room 9.

As described above, according to this embodiment, since the solid sample 18 is introduced into the reserve room 9 from the exterior through the inlet 21 while the purge gas 20 is jetted out from the reserve room 9, contaminants included in the external air are prevented from entering the reserve room 9 from the exterior and attaching to the inner surface of the reserve room 9.

Since the reserve room 9 is preliminarily heated by the preliminary heater 22 and contaminants attaching to the inner surface of the reserve room 9 are expelled, contaminants attaching to the inner surface of the reserve room 9 can be removed before the introduction of the solid sample 18.

Embodiment 3

Figure 5:
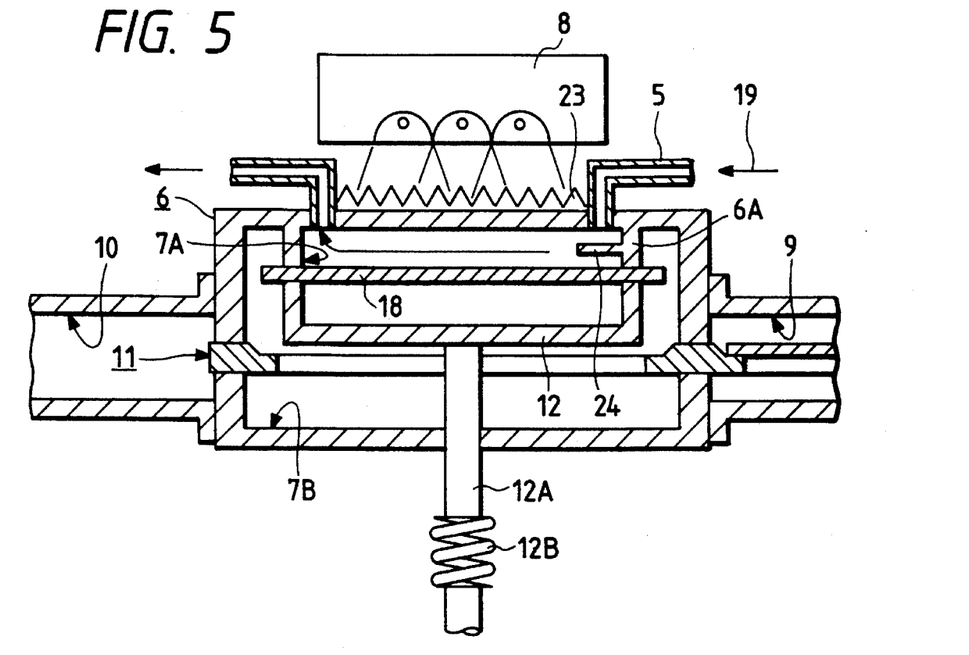
FIG. 5 is a schematic diagram showing a general configuration of an atmospheric pressure, elevated temperature gas desorption apparatus according to a third embodiment of the invention.

FIG. 5 (schematic diagram) shows a general configuration of an atmospheric pressure, elevated temperature gas desorption apparatus which is a third embodiment of the invention.

As shown in FIG. 5, as in the case of the first embodiment, the atmospheric pressure, elevated temperature gas desorption apparatus of this embodiment has a chamber 6, a desorption room 7A, a sample support room 7B, a heater 8, reserve rooms 9 and 10, a conveyor 11, a sample support 12, and other parts.

The heater 8 is constituted of an infrared lamp. An infrared diffusing member 23 for transmitting infrared light while diffusing it uniformly is disposed between the heater 8 and the desorption room 7A.

A spring mechanism 12B is provided in a support member 12A that is fixed to the sample support 12, to make uniform a force of bringing the solid sample 18 into close contact with the partition member 6A.

A gas diffusing member 24 for diffusing a carrier gas 19 that is supplied from a gas supply system is provided in the desorption room 7A.

The atmospheric pressure, elevated temperature gas desorption apparatus having the above configuration operates in the following manner. The solid sample 18 conveyed into the sample support room 7B is made in close contact with the partition member 6A by the sample support 12 so that the desorption room 7A is separated from the sample support room 7B by the partition member 6A and the solid sample 18. In this state, the pressure of the carrier gas 19 supplied to the desorption room 7A is made higher than the gas pressure in the sample support room 7B. As a result, the carrier gas 19 is jetted out from the desorption room 7A at about 1 L/min through the closecontact portion, to prevent gas entrance from the sample support room 7B to the desorption room 7A.

On the other hand, when the carrier gas 19 is supplied to the desorption room 7A through the pipe 5, it is diffused by the gas diffusing member 24 and impinges on the one surface of the solid sample 18 uniformly. In this state, the solid sample 18 is heated with infrared light from the heater 8. The infrared light is diffused by the infrared diffusing member 23, and strikes the one surface of the solid sample 18 uniformly. Therefore, the one surface of the solid sample 18 has a uniform temperature distribution.

As described above, according to this embodiment, since the infrared light uniformly illuminates the surface of the solid sample 18, a variation in the temperature distribution of the solid sample 18 can be reduced. Therefore, it becomes possible to correctly perform the quantitative analysis of impurities absorbed in or on the surface of the solid sample Further, since the carrier gas 19 is diffused by the gas diffusing member 24 and impinges on the surface of the solid sample 18 uniformly, a variation in the temperature distribution of the solid sample 18 can be reduced. This also helps correctly perform the quantitative analysis of impurities absorbed in or on the surface of the solid sample 18.

Embodiment 4

Figure 6:
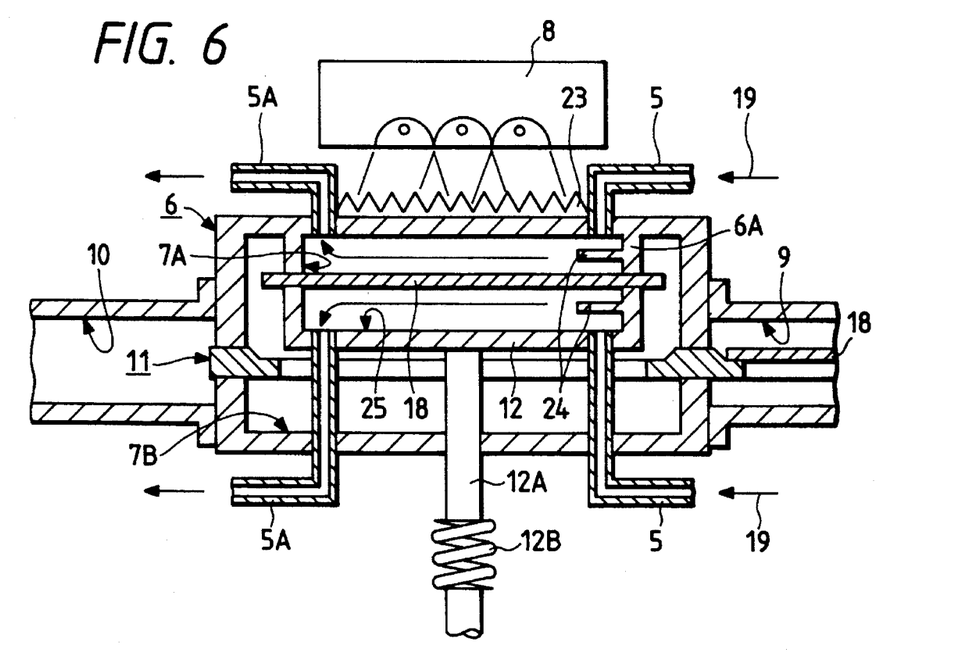
FIG. 6 is a schematic diagram showing a general configuration of an atmospheric pressure, elevated temperature gas desorption apparatus according to a fourth embodiment of the invention

FIG. 6 (schematic diagram) shows a general configuration of an atmospheric pressure, elevated temperature gas desorption apparatus which is a fourth embodiment of the invention.

As shown in FIG. 6, the atmospheric pressure, elevated temperature gas desorption apparatus of this embodiment has a chamber 6, a desorption room 7A, a sample support room 7B, a heater 8, reserve rooms 9 and 10, a conveyor 11, a sample support 12, a desorption room 25, and other parts.

The desorption room 7A is separated from the sample support room 7B by the partition member 6A and the solid sample 18 being in close contact with the partition member 6A. A pipe 5 for introducing a carrier gas 19 from a gas supply system to the desorption room 7A and a pipe 5A for introducing the carrier gas 19 including impurities desorbed from the surface of the solid sample 18 to, for instance, an analyzer are connected to the desorption room 7A.

The desorption room 25 is separated from the sample support room 7B by the sample support 12 having a concave sectional shape and the solid sample 18 supported by the sample support 12. The desorption rooms 25 and 7A are separated from each other by the solid sample 18.

A pipe 5 for introducing the carrier gas 19 from the gas supply system to the desorption room 25 and a pipe 5A for introducing the carrier gas 19 including impurities desorbed from the surface of the solid sample 18 to, for instance, the analyzer are connected to the desorption room 25. The pipes 5 and 5A connected to the desorption room 25 are fixed to the sample support 12 so as to be movable together with the sample support 12.

The atmospheric pressure, elevated temperature gas desorption apparatus having the above configuration operates in the following manner. The sample support 12 makes the solid sample 18 in close contact with the partition member 6A so that the solid sample 18 separates the desorption rooms 7A and 25 from each other and also separates each of the desorption rooms 7A and 25 from the sample support room 7B. In this state, the pressure of the carrier gas 19 supplied to the desorption rooms 7A and 25 is made higher than the gas pressure in the sample support room 7B. As a result, the carrier gas 19 is jetted out from each of the desorption rooms 7A and 25 at about 1 L/min through the close-contact portion, to prevent gas entrance from the sample support room 7B to the desorption rooms 7A and 25.

As described above, according to this embodiment, impurities absorbed in or on the front surface of the solid sample 18 are desorbed into the one carrier gas 19 while impurities absorbed in or on the back surface of the solid sample 18 are desorbed into the other carrier gas 19. Therefore, impurities absorbed in or on the front and back surfaces of the solid sample 18 can be desorbed separately.

Embodiment 5

Figure 7:
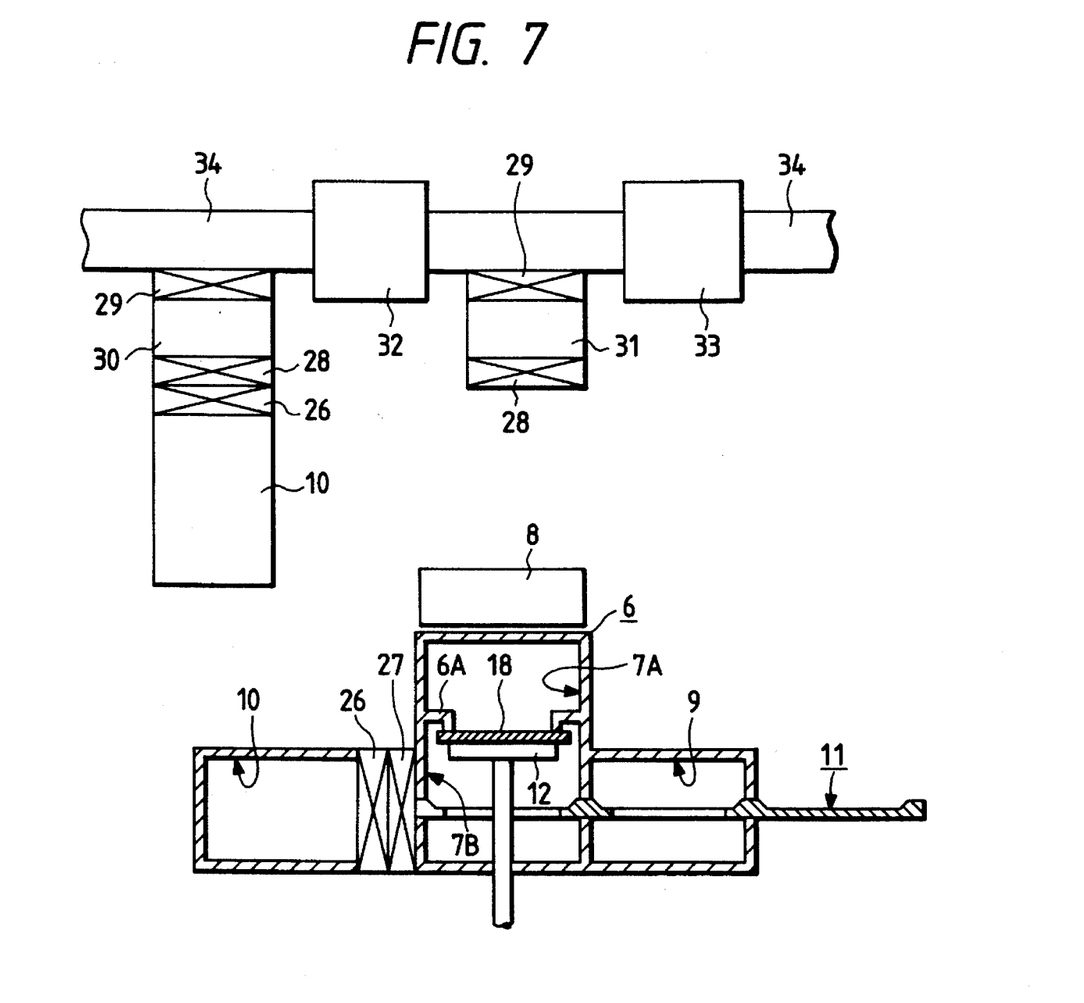
FIG. 7 is a schematic diagram showing a relationship between a manufacturing process line and an atmospheric pressure elevated temperature gas desorption apparatus according to a fifth embodiment of the invention.

FIG. 7 (schematic diagram) shows a relationship between a manufacturing process line and an atmospheric pressure, elevated temperature gas desorption apparatus according to a fifth embodiment of the invention.

As shown in FIG. 7, the atmospheric pressure, elevated temperature gas desorption apparatus according to this embodiment has shutters 26 and 27 between the sample support room 7B and the reserve room 10 so that the reserve room 10 can be separated from the sample support room 7B. In FIG. 7, reference numeral 34 denotes a manufacturing process line, and numerals 33 and 32 are manufacturing processes such as cleaning and drying that are included in the manufacturing process line 34. Intermediate rooms 30 and 31 are connected to the manufacturing process line through shutters 29. A shutter 28 is provided in each of the intermediate rooms 30 and 31.

The apparatus of this embodiment operates in the following manner. After a solid sample 18 for preliminary heating is brought in close contact with the partition member 6A and the desorption room 7A is thereby separated from the sample support room 7B, the shutters 26 and 27 are closed.

Then, the reserve room 10 including the shutter 26 is removed (detached) from the shutter 27, and is connected to the intermediate room 30 or 31 through the shutter 28. At this stage, the shutters 28 and 29 are closed.

Then, the purge gas 20 is supplied to the intermediate room 30.

Then, after the shutter 29 is opened and a solid sample 18 for analysis is introduced from the manufacturing process 32 to the intermediate room 30, the shutter 29 is closed. Thereafter, the purge gas 20 is again supplied to the intermediate room 30 so that an atmosphere of the manufacturing process 32 does not influence the intermediate room 30.

Then, the shutters 28 and 26 are opened and the solid sample 18 for analysis is introduced into the reserve room 10. The shutters 28 and 26 are thereafter closed.

Then, the reserve room 10 is detached from the intermediate room 30, and again connected to the sample support room 7B.

Then, preliminary heating is performed by the heater 8. After contaminants attaching to the inner surface of the desorption room 7A are thereby removed, the shutters 26 and 27 are opened and the solid sample 18 is conveyed from the reserve room 10 to the sample support room 7B by the conveyor 11.

Finally, the solid sample 18 is heated by the heater 8 while being made in close contact with the partition member 6A by the sample support 12, to desorb impurities (minute substances) absorbed in or on the one surface of the solid sample 18.

As described above, according to this embodiment, the solid sample 18 for analysis can be introduced from each manufacturing process included the manufacturing process line to the sample support room 7B without being exposed to the external air. Therefore, impurities (minute substances) absorbed in or on the one surface of the solid sample 18 can be desorbed without being influenced by the background due to contaminants of the external air. This enables the quantitative analysis of impurities absorbed in or on the surface of the solid sample 18 to be performed correctly.

Embodiment 6

Figure 8:
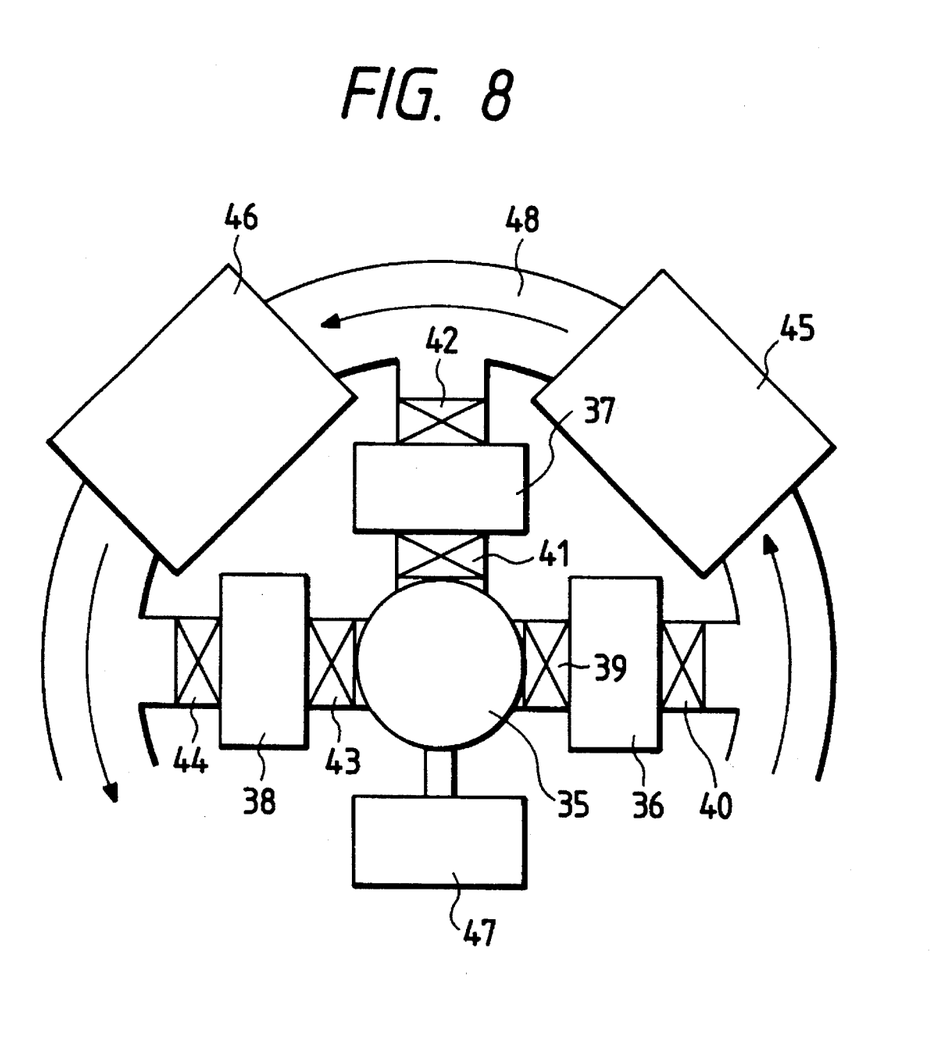
FIG. 8 is a schematic diagram showing a general configuration of an atmospheric pressure, elevated temperature gas desorption apparatus according to a sixth embodiment of the invention.

FIG. 8 (schematic diagram) shows a general configuration of an atmospheric pressure, elevated temperature gas desorption apparatus according to a sixth embodiment of the invention.

As shown in FIG. 8, in the atmospheric pressure, elevated temperature gas desorption apparatus of this embodiment, reserve rooms 36–38 are connected to a chamber 35 through shutters 39, 41 and 43, respectively. Further, the reserve rooms 36-38 are connected to a manufacturing process line 48 through shutters 40, 42 and 44, respectively. In FIG. 8, reference numerals 45 and 46 denote manufacturing processes such as cleaning and drying included in the manufacturing process line 48, and numeral 47 denotes an analyzer for analyzing impurities absorbed in or on the surface of a solid sample placed in the chamber 35.

The apparatus of this embodiment operates in the following manner. A solid sample (18) for analysis is conveyed along the manufacturing process line 48 is introduced into the reserve room 36 through the opened shutter 40. Then, the shutter 40 is closed and a purge gas is supplied to the reserve room 36. After the supplying of the purge gas to the reserve room 36, the shutter 39 is opened to introduce the solid sample for analysis into the chamber 35. The shutter 39 is thereafter closed, and impurities absorbed on or in the surface of the solid sample for analysis are desorbed into a carrier gas. Impurities absorbed in or on the solid sample are analyzed by analyzing the carrier gas including impurities thus desorbed with the analyzer 47.

Then, the shutter 39 is opened, and the solid sample for analysis is returned from the chamber 35 to the reserve room 36. The shutter 39 is thereafter closed, and the shutter 40 is opened to return the solid sample from the reserve room 36 to the manufacturing process line 48. The solid sample thus placed on the manufacturing process line 48 is processed by the manufacturing process 45, and again returned to the manufacturing process line 48.

The solid sample for analysis as processed by the manufacturing process 45 is introduced into the reserve room 37 through the opened shutter 42. The shutter 42 is thereafter closed, and the purge gas is supplied to the reserve room 37. After the supplying of the purge gas to the reserve room 37, the shutter 41 is opened to introduce the solid sample for analysis into the chamber 35. The shutter 41 is thereafter closed, and impurities absorbed on or in the surface of the solid sample for analysis are desorbed into a carrier gas. Then, as in the above operation, the solid sample for analysis is returned from the chamber 35 to the manufacturing process line 48 by operating the shutters 41 and 42.

The solid sample thus placed on the manufacturing process line 48 is processed by the manufacturing process 46, and again returned to the manufacturing process 48.

The solid sample as processed by the manufacturing process 46 is introduced into the reserve room 38 through the opened shutter 44. Thereafter, as in the above operations, impurities absorbed in or on the surface of the solid sample as processed by the manufacturing process 46 are desorbed into a carrier gas and analyzed by the analyzer 47.

As described above, according to this embodiment, the respective manufacturing processes are arranged around the chamber 35, and the solid sample 18 for analysis is directly conveyed to the chamber 35 before and after being subjected to each manufacturing process through proper ones of the reserve rooms 36–38. Since in this manner the quantitative analysis on impurities absorbed in or on the surface of the solid sample 18 can be performed correctly before and after each manufacturing process, contamination or the like of the solid sample 18 due to each manufacturing process can be examined.

Embodiment 7

Figure 9:
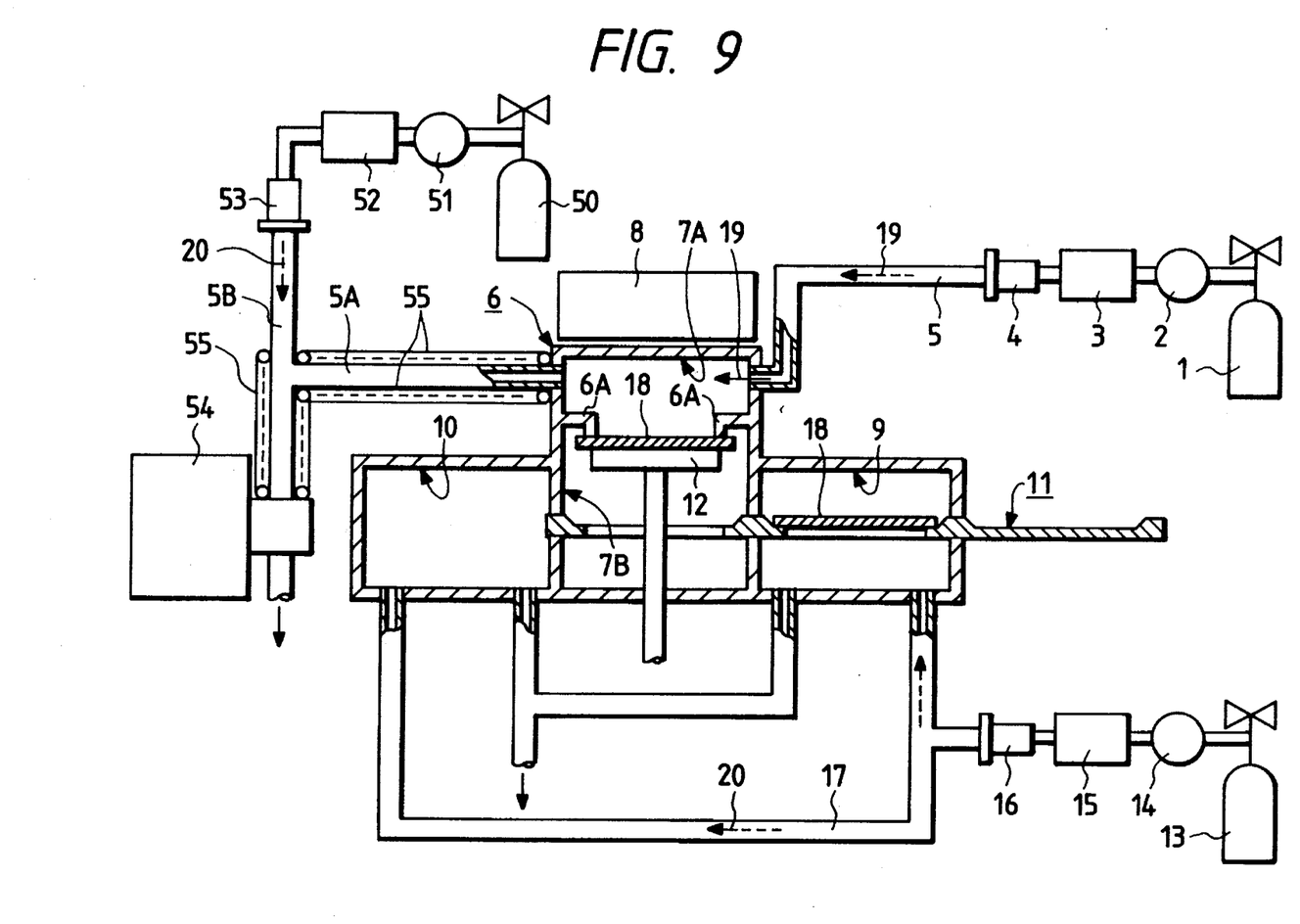
FIG. 9 is a schematic diagram showing a general configuration of an atmospheric pressure, elevated temperature gas desorption apparatus according to a seventh embodiment of the invention.

FIG. 9 (schematic diagram) shows a general configuration of an atmospheric pressure, elevated temperature gas desorption apparatus which is a seventh embodiment of the invention.

As shown in FIG. 9, the atmospheric pressure, elevated temperature gas desorption apparatus of this embodiment has a gas supply system 1 (a pure gas cylinder), a pressure regulator 2, a flow rate regulator 3, a molecular sieve trap 4, a chamber 6, a desorption room 7A, a sample support room 7B, a heater 8, reserve rooms 9 and 10, a conveyor 11, a sample support 12, a gas supply system 13 (pure gas cylinder), a pressure regulator 14, a flow rate regulator 15, a molecular sieve trap 16, a gas supply system 50 (a pure gas cylinder), a pressure regulator 51, a flow rate regulator 52, a molecular sieve trap 53, an analyzer 54, a pipe heater 55, and other parts.

The desorption room 7A is connected to the analyzer 54 through a pipe 5A. To supply a purge gas 20 to the analyzer 54, the gas supply system 50 is connected to the analyzer through a pipe 5B and the pipe 5A. The gas supply system 50 supplies the purge gas 20 to prevent that a gas within the sample support room 7B flows into the analyzer 54 when the close contact between the partition member 6A and the solid sample 18 is released.

The pressure regulator 51, flow rate regulator 52 and molecular sieve trap 53 are attached to the pipe 5B. The pressure regulator 51 keeps the purge gas 20 at a constant pressure, and the flow rate regulator 52 keeps it at a constant flow rate. The molecular sieve trap 53 removes impurities such as moisture and organic substances from the purge gas 20.

The analyzer 54 analyzes impurities included in a carrier gas 19 that have been desorbed in the desorption room 7A. The analyzer 54 is an atmospheric pressure ionization mass spectroscope, a gas chromatograph, a gas chromatograph mass spectroscope, or the like.

The pipe heater 55 is attached to the pipe 5A, and heats the pipe 5A to prevent impurities that have been desorbed into the carrier gas 19 in the desorption room 7A from sticking to the inner surface of the pipe 5A.

The atmospheric pressure, elevated temperature gas desorption apparatus having the above configuration operates in the following manner. First, the carrier gas 19 is supplied from the gas supply system 1 to the desorption room 7A through the pipe 5. The pressure and flow rate of the carrier gas 19 are respectively regulated to constant values by the pressure regulator 2 and the flow rate regulator 3, and impurities such as moisture and organic substances are removed from the carrier gas 19 by the molecular sieve trap 4.

Then, a solid sample 18 to be used for preliminary heating is made in close contact with the partition member 6A by the sample support 12 to separate the desorption room 7A from the sample support room 7B. In this state, another solid sample 18 to be used for analysis is reserved in the reserve room 9. The purge gas 20 is supplied from the gas supply system 13 to the reserve rooms 9 and 10 through a gas pipe 17. The pressure and flow rate of the purge gas 20 are respectively regulated to constant values by the pressure regulator 14 and the flow rate regulator 15, and impurities such as moisture and organic substances are removed from the purge gas 20 by the molecular sieve trap 16.

Then, in the state that the desorption room 7A is separated from the sample support room 7B by the solid sample 18 for preliminary heating and the solid sample 18 for analysis stands by in the reserve room 9, the preliminary heating is performed by the heater 8. The preliminary heating serves to remove impurities attaching to the inner surfaces of the chamber 6 (desorption room 7A and sample support room 7B). The temperature of the solid sample 18 for preliminary heating is thereafter reduced to the room temperature (normal temperature).

Then, after the sample support 12 is lowered and the solid sample 18 for preliminary heating is mounted on the mounting region 11A of the conveyor 11, the conveyor 11 is moved so as to forward the solid sample 18 for preliminary heating to the reserve room 10 and introduce the solid sample 18 for analysis into the sample support room 7B.

Then, the sample support 12 is elevated to make the solid sample 18 for analysis in close contact with the partition member 6A. In this state, heating is performed by the heater 8 to desorb impurities that are absorbed in or on the one surface of the solid sample 18 for analysis into the carrier gas 19.

Then, the carrier gas 19 as subjected to the desorption is supplied to the analyzer through the pipe 5A. At this time, since the pipe 5A is heated by the pipe heater 55, it can be prevented that impurities included in the carrier gas 19 attach to the inner surface of the pipe 5A.

As described above, according to this embodiment, the carrier gas 19 including impurities as desorbed from the solid sample 18 can be supplied to the analyzer 54 without being influenced by the background due to contaminants attaching to the inner surfaces of the chamber 6, pipe 5A, etc. Therefore, the quantitative analysis of impurities absorbed in or on the surface of the solid sample 18 can be performed correctly.

Embodiment 9

Figure 10:
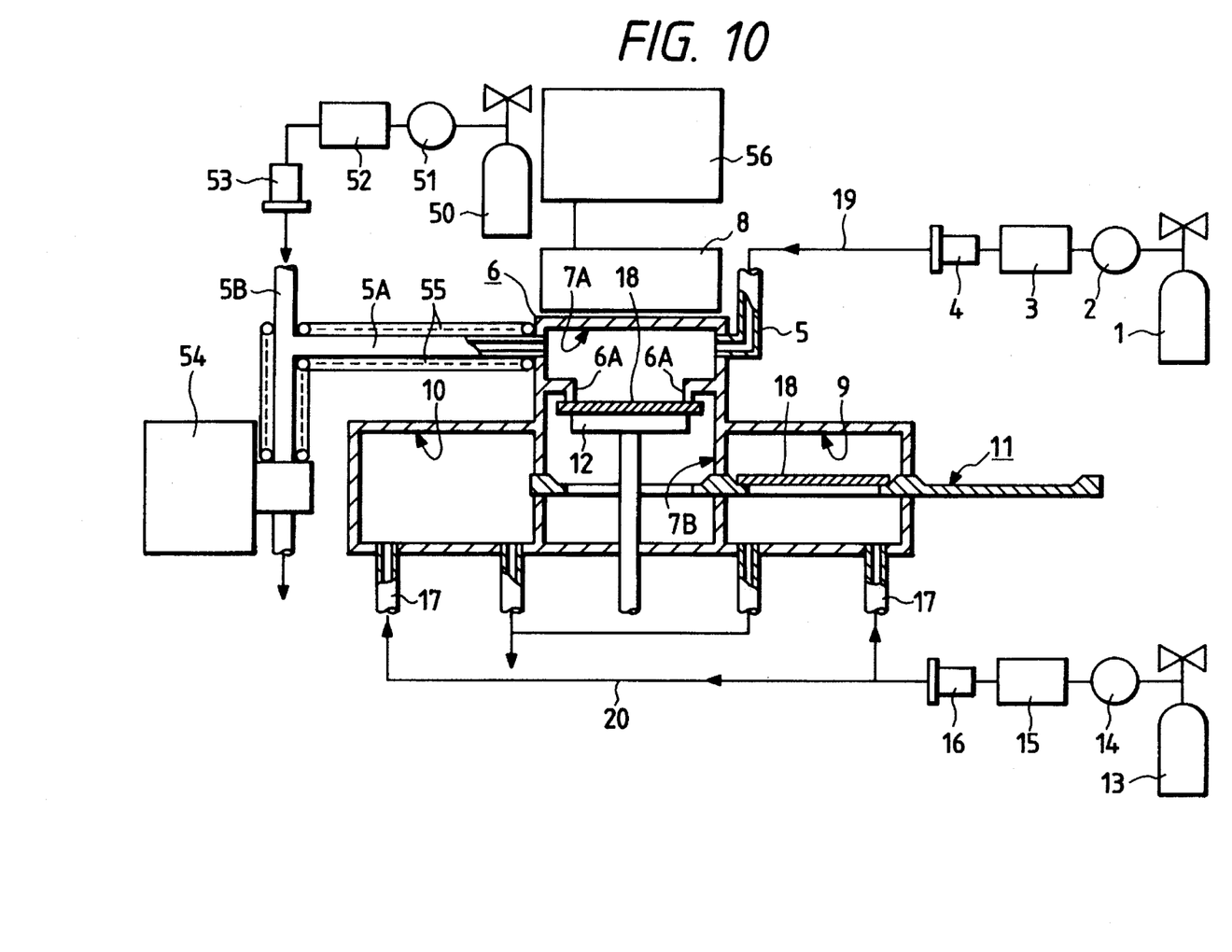
FIG. 10 is a schematic diagram showing a general configuration of an atmospheric pressure, elevated temperature gas desorption apparatus according to an eighth embodiment of the invention.

FIG. 10 (schematic diagram) shows a general configuration of an atmospheric pressure, elevated temperature gas desorption apparatus according to a ninth embodiment of the invention.

Figure 11:
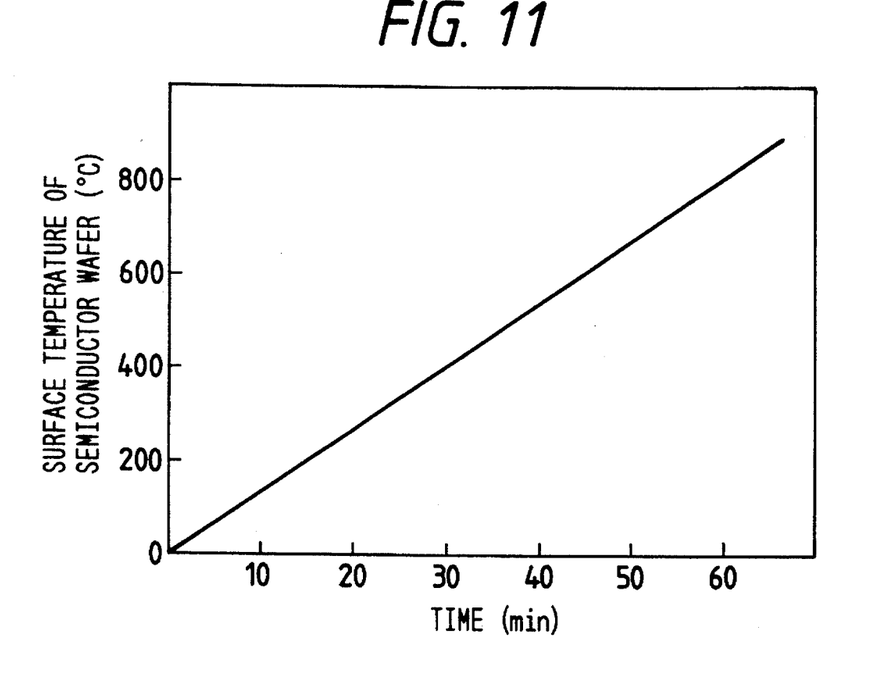
FIGS. 11 and 12 are graphs showing relationships between time and a temperature of a solid sample.
Figure 12:
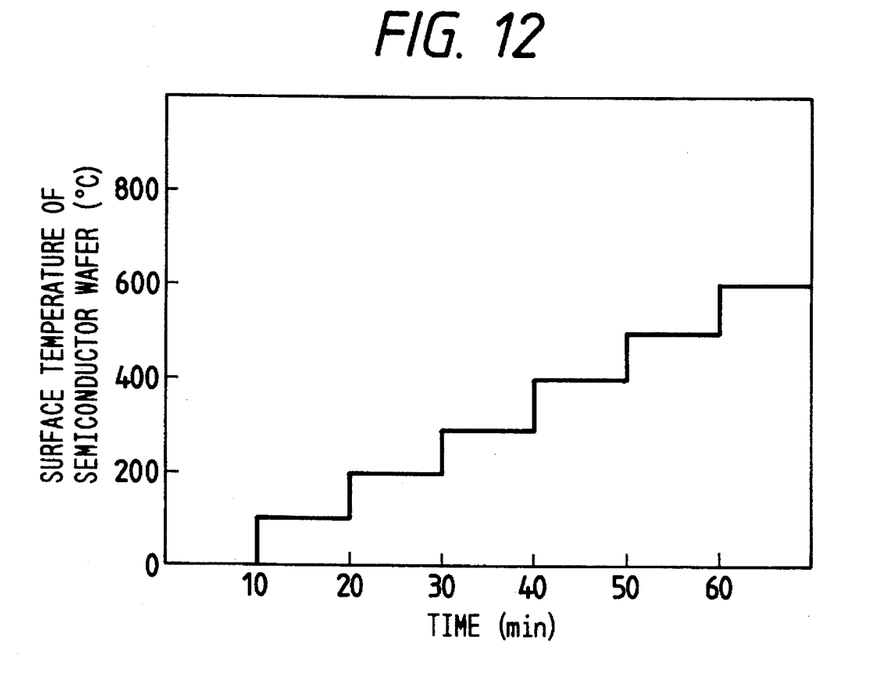

In FIG. 10, reference numeral 56 denotes an external computer for controlling the temperature of the heater 8. The apparatus of this embodiment operates in the following manner. After a solid sample 18 for analysis is brought in close contact with the partition member 6A, it is heated by the infrared lamp of the heater 8. In this case, the temperature control is performed in which a temperature increasing pattern of the solid sample 18 is selected by the external computer 56. Substances of a very small amount absorbed in or on the one surface of the solid sample 18 are desorbed at a controlled temperature, introduced to an atmospheric pressure ionization mass spectroscope 54, and subjected to qualitative and quantitative analyses therein. FIGS. 11 and 12 show relationships between time and the temperature of the solid sample 18.

According to this embodiment, the temperature increasing pattern can be selected as desired by the external computer 56; for instance, a step-like pattern (FIG. 12) is used for detecting a very small peak, and a fixed rate increasing pattern (FIG. 11) is used for examining a relationship between peak locations and temperature. Therefore, it is possible to perform qualitative and quantitative analyses of substances of a very small amount that are absorbed in or on the one surface of the solid sample 18.

Embodiment 10

Figure 13:
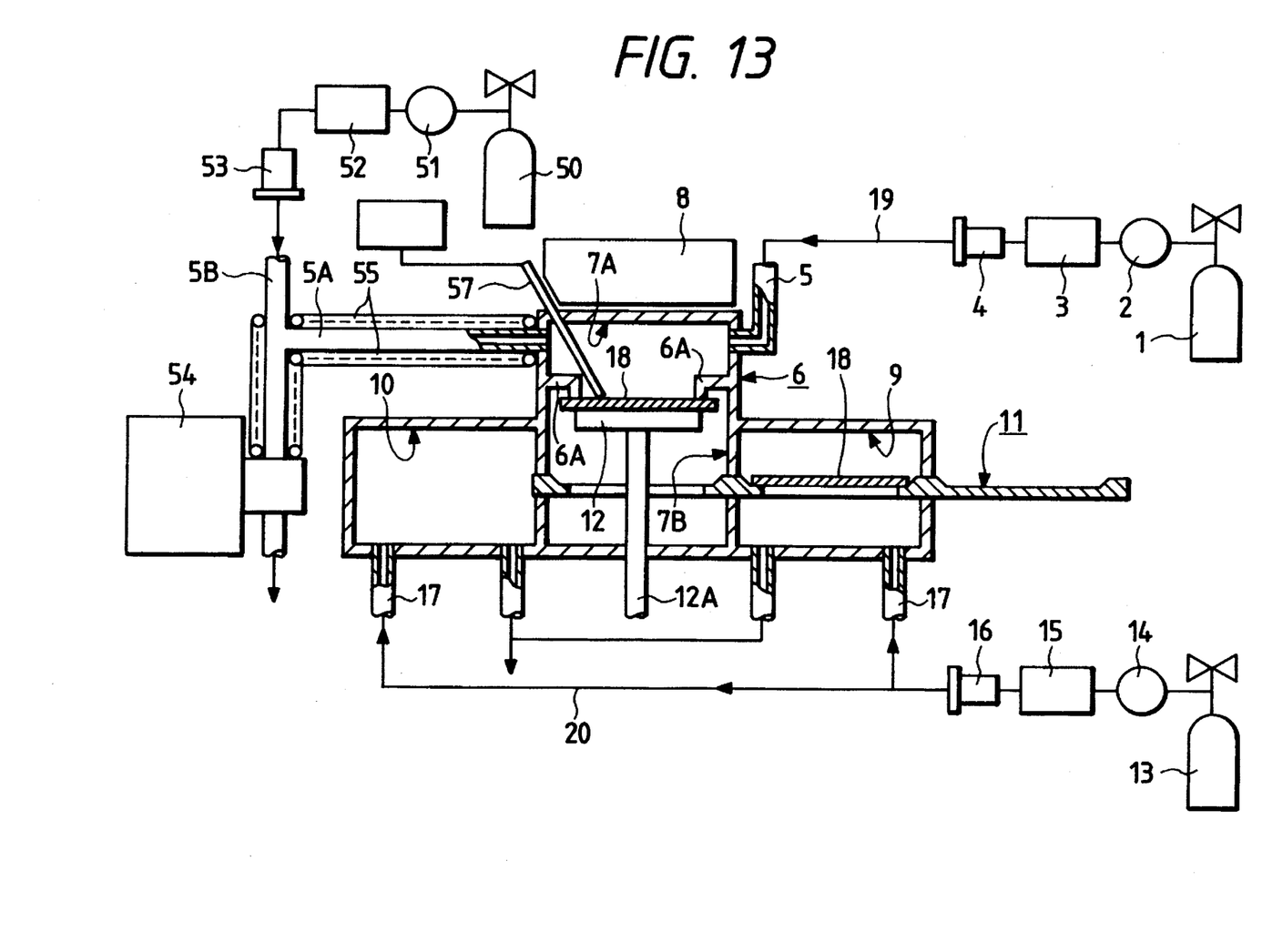
FIG. 13 is a schematic diagram showing a general configuration of an atmospheric pressure, elevated temperature gas desorption apparatus according to a ninth embodiment of the invention.

FIG. 13 (schematic diagram) shows a general configuration of an atmospheric pressure, elevated temperature gas desorption apparatus according to a tenth embodiment of the invention.

In FIG. 13, reference numeral 57 denotes a surface measuring probe for observing variations in shape and state of the one surface of a heated solid sample 18.

The apparatus of this embodiment operates in the following manner. After the solid sample 18 for analysis is brought in close contact with the partition member 6A, it is heated by the infrared lamp of the heater 8. When substances of a very small amount that are absorbed in or on the one surface of the solid sample 18 are desorbed from it, the shape and state of the surface of the solid sample 18 change. While the variations in shape and state are observed by the surface measuring probe 57, released substances of a very small amount are introduced to an atmospheric pressure ionization mass spectroscope 54 and subjected to qualitative and quantitative analyses therein.

As described above, according to this embodiment, not only the qualitative and quantitative analyses of substances of a very small amount absorbed in or on the one surface of the solid sample 18 can be performed, but also the shape and state of the surface of the solid sample 18 can be observed at the same temperature. Therefore, it becomes possible to examine a correlation between the temperature, released substances and the surface state of the solid sample 18.

Embodiment 11

Figure 14:
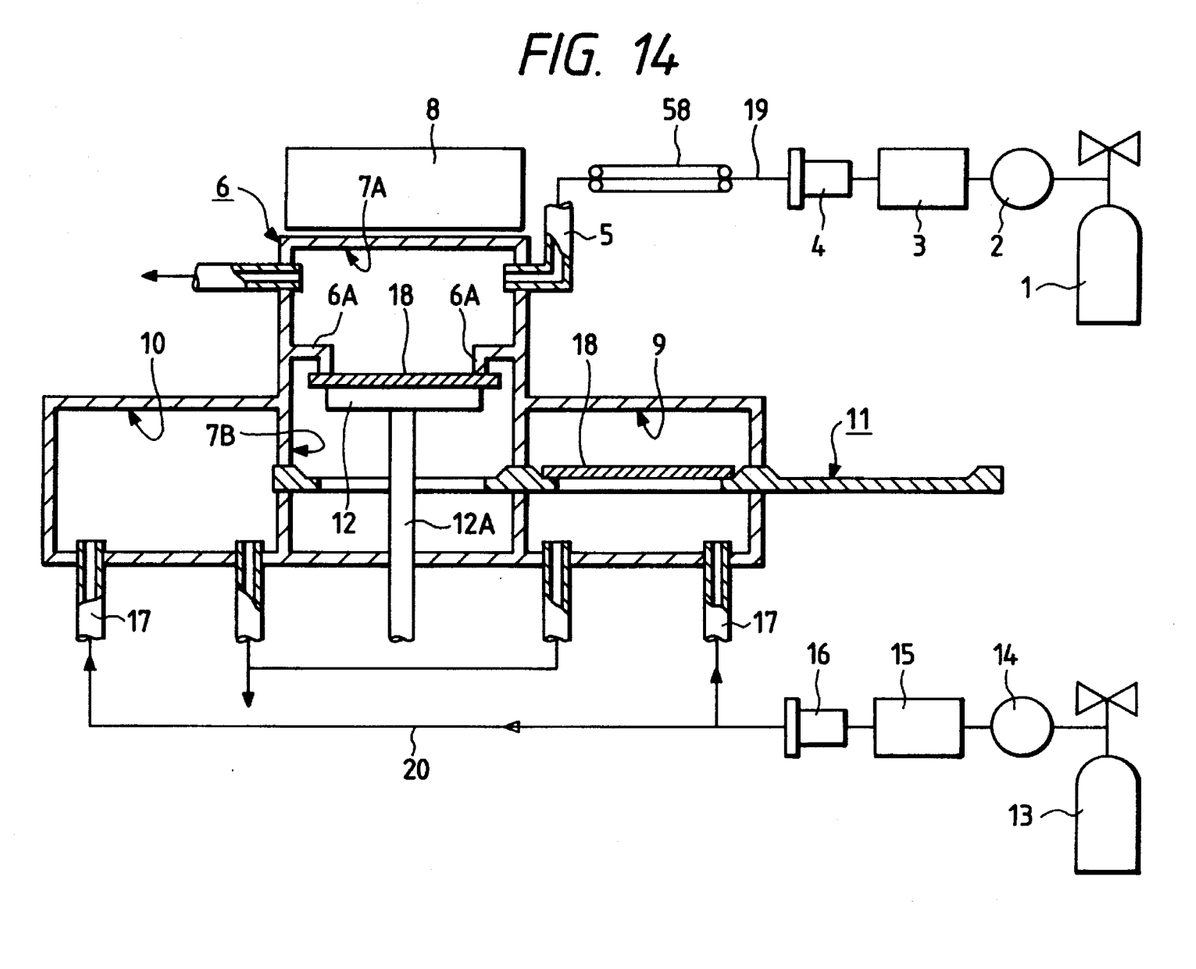
FIG. 14 is a schematic diagram showing a general configuration of an atmospheric pressure, elevated temperature gas desorption apparatus according to a tenth embodiment of the invention.

FIG. 14 (schematic diagram) shows a general configuration of an atmospheric pressure, elevated temperature gas desorption apparatus according to an eleventh embodiment of the invention.

In FIG. 14, reference numeral 58 denotes a heater for heating a carrier gas 19 to be supplied to a chamber 6.

The apparatus of this embodiment operates in the following manner. The heater 58 heats the carrier gas 19 to be supplied from the gas supply system 1 to the chamber 6 through the gas pipe 5.

As described above, according to this embodiment, since the carrier gas 19 that has been heated to a predetermined temperature is supplied to the chamber 6, it does not cool one surface of the solid sample 18. Therefore, impurities absorbed in or on the surface of the solid sample 18 can be desorbed into the carrier gas 19 with an improved resolution of setting the temperature of the solid sample 18.

Although the invention made by the present inventors has been described in a specific manner based on the embodiments, it is apparent that the invention is in no way limited to those embodiments but various modification are possible without departing from the scope and spirit of the invention.

Advantages obtained by a representative parts of the invention disclosed in this application will be briefly described below.

(1) Since impurities are desorbed from a solid sample in its original state (i.e., not divided into small pieces), the quantitative analysis of impurities absorbed in or on the surface of the solid sample can be performed correctly.

(2) Since impurities absorbed in or on the surface of a solid sample are desorbed after contaminants attaching to the inner surfaces of the chamber are removed, the quantitative analysis of impurities absorbed in or on the surface of the solid sample can be performed correctly without being influenced by the external air.

(3) Since variations in a temperature distribution of a solid sample can be reduced, the quantitative analysis of impurities absorbed in or on the surface of the solid sample can be performed correctly.

(4) Since the front surface and the back surface of a solid sample can be processed separately, the quantitative analysis of impurities absorbed in or on the surface of the solid sample can be performed correctly.

(5) Impurities absorbed in or on the front surface of a solid sample and those absorbed in or on its back surface can be desorbed separately.

What is claimed is:

1. An atmospheric pressure, elevated temperature gas desorption apparatus for desorbing impurities absorbed in or on a surface of a plate-like solid sample into a carrier gas in a chamber under an atmospheric pressure while increasing the temperature of the solid sample, said apparatus comprising:

a desorption room provided in the chamber and connected through a pipe to a first gas supply system for supplying the carrier gas, for desorbing impurities absorbed in or on the surface of the solid sample into the carrier gas supplied from the first gas supply system;

a sample support room provided in the chamber and to be separated from the desorption room by a partition member and the solid sample being brought in close contact with the partition member, for incorporating a sample support for conveying and supporting the solid sample to be brought in close contact with the partition member;

a heater for heating the solid sample being in close contact with the partition member; and a reserve room connected to the sample support room and connected through a supply pipe to a second gas supply system for supplying a purge gas, for reserving the solid sample to be conveyed to the sample support room.

2. The atmospheric pressure, elevated temperature gas desorption apparatus according to claim 1, wherein the reserve room has a inlet for introducing the solid sample from the exterior, the inlet having such a size that it allows a clearance around the solid sample.

3. The atmospheric pressure, elevated temperature gas desorption apparatus according to claim 2, wherein the heater includes an infrared lamp, and wherein an infrared light diffusing plate is disposed between the infrared lamp and the desorption room.

4. The atmospheric pressure, elevated temperature gas desorption apparatus according to claim 2, wherein a gas diffusing member for diffusing the carrier gas is disposed in the desorption room in the vicinity of the pipe through which the carrier gas is supplied.

5. The atmospheric pressure, elevated temperature gas desorption apparatus according to claim 2, wherein first and second shutters are provided for the reserve room and the sample support room, respectively to separate those rooms from each other.

6. The atmospheric pressure, elevated temperature gas desorption apparatus according to claim 1, wherein the heater includes an infrared lamp, and wherein an infrared light diffusing plate is disposed between the infrared lamp and the desorption room.

7. The atmospheric pressure, elevated temperature gas desorption apparatus according to claim 6, wherein a gas diffusing member for diffusing the carrier gas is disposed in the desorption room in the vicinity of the pipe through which the carrier gas is supplied.

8. The atmospheric pressure, elevated temperature gas desorption apparatus according to claim 6, wherein first and second shutters are provided for the reserve room and the sample support room, respectively to separate those rooms from each other.

9. The atmospheric pressure, elevated temperature gas desorption apparatus according to claim 1, wherein a gas diffusing member for diffusing the carrier gas is disposed in the desorption room in the vicinity of the pipe through which the carrier gas is supplied.

10. The atmospheric pressure, elevated temperature gas desorption apparatus according to claim 9, wherein first and second shutters are provided for the reserve room and the sample support room, respectively to separate those rooms from each other.

11. The atmospheric pressure, elevated temperature gas desorption apparatus according to claim 1, wherein first and second shutters are provided for the reserve room and the sample support room, respectively to separate those rooms from each other.

12. An atmospheric pressure, elevated temperature gas desorption apparatus for desorbing impurities absorbed in or on a surface of a plate-like solid sample into a carrier gas in a chamber under an atmospheric pressure while increasing a temperature of the solid sample, said apparatus comprising:

a first desorption room provided in the chamber and connected through a first pipe to a gas supply system for supplying the carrier gas, for desorbing impurities absorbed in or on a front surface of the solid sample into the carrier gas supplied from the gas supply system;

a second desorption room provided in the chamber, to be separated from the first desorption room by a partition member and the solid sample being brought in close contact with the partition member, and connected through a second pipe to the gas supply system for supplying the carrier gas, for desorbing impurities absorbed in or on a back surface of the solid sample that is opposed to the front surface into the carrier gas supplied from the gas supply system; and a heater for heating the solid sample being brought in close contact with the partition member.

* * * * *